(12) United States Patent
Descamps-Francois et al.

(10) Patent No.: US 7,161,035 B2
(45) Date of Patent: Jan. 9, 2007

(54) SUBSTITUTED BIPHENYL DERIVATIVES, METHOD FOR PREPARING SAME AND PHARMACEUTICAL COMPOSITIONS CONTAINING SAME

(75) Inventors: Carole Descamps-Francois, Hellemes (FR); Said Yous, Loos (FR); Daniel Lesieur, Gondecourt (FR); Gérald Guillaumet, Saint Jean le Blanc (FR); Marie-Claude Viaud, Tours (FR); Hervé Da Costa, Chambray les Tours (FR); Caroline Bennejean, Charenton le Pont (FR); Philippe Delagrange, Issy les Moulineaux (FR); Pierre Renard, Le Chesnay (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 296 days.

(21) Appl. No.: 10/380,866

(22) PCT Filed: Jul. 16, 2001

(86) PCT No.: PCT/FR01/02297

§ 371 (c)(1), (2), (4) Date: Mar. 14, 2003

(87) PCT Pub. No.: WO02/22555

PCT Pub. Date: Mar. 21, 2002

(65) Prior Publication Data

US 2004/0014969 A1 Jan. 22, 2004

(30) Foreign Application Priority Data

Sep. 15, 2000 (FR) .................................. 00 11779

(51) Int. Cl.
C07C 233/00 (2006.01)
(52) U.S. Cl. ........................ 564/192; 514/617; 514/625
(58) Field of Classification Search ................ 568/172; 514/617
See application file for complete search history.

(56) References Cited

U.S. PATENT DOCUMENTS

| 5,093,352 A | 3/1992 | Dubocovich |
| 5,922,771 A | 7/1999 | Fukatsu et al. |

FOREIGN PATENT DOCUMENTS

| EP | 0919541 | 6/1999 |
| EP | 0926145 | 6/1999 |
| EP | 0994102 | 4/2000 |
| FR | 2778662 | 11/1999 |
| WO | WO 97/38682 | 10/1997 |

OTHER PUBLICATIONS

Li, et al., *Drugs of the Future*, 2000, 25, 945-957.
Krause, et al., *Society Neuroscience*, 1996, 22, No. 651.19, p. 1400.
Vacas, et al., *J. Pineal Research*, 1992, 13, 60-65.
Cagnacci, et al., *J. Pineal Research*, 1997, 22, 16-19.
Lagneux, et al., *Life Sciences*, 2000, 66, 503-509.
Brydon, et al., *Endocrinology*, 2001, 142, 4264-4271.
Bylesjö, et al., *International Journal of Eating Disorders*, 1996, 20, 443-446.
Ferrari, et al., *Biol. Psychiatry*, 1990, 27, 1007-1020.
Mazzucchelli, et al., *Molecular Brain Research*, 1996, 39, 117-126.
Brown, *CNS Drugs*, 1995, 3, 209-226.
Skene, et al., *Brain Research*, 1990, 528, 170-174.
Monteleone, et al., *Schizophrenia Research*, 1992, 7, 77-84.
Mc Intyre, et al., *Journal of Affective Disorders*, 1987, 12, 203-206.
Erlich, et al., *J. Neurosurg.*, 1985, 63, 321-341.
Maurizi, *Medical Hypotheses*, 1988, 27, 271-276.
Kopp, et al., *Behavioural Pharmacology*, 1999, 10, 73-83.
Kopp, et al., *Neuorpharmacology*, 2000, 39, 1865-1871.

(Continued)

Primary Examiner—Amelia A. Owens
(74) Attorney, Agent, or Firm—Hueschen and Sage

(57) ABSTRACT

The invention relates to compounds of formula (I):

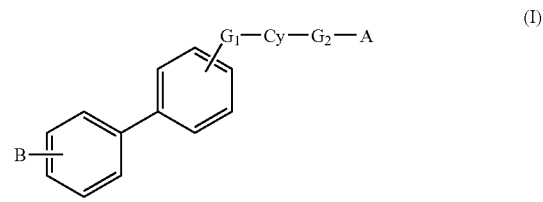

wherein:
B represents a hydrogen atom, a COOR group, a CONRR' group, or a ($C_1$–$C_6$)alkyl group substituted by a COOR, CONRR' or OR group,
$G_1$ represents a —X'—$(CH_2)_n$—X—$(CH_2)_m$—X"— chain wherein X, X', X", n and m are as defined in the description,
Cy represents a grouping of formula (II) or (III):

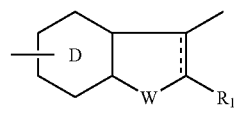

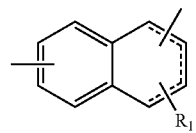

$G_2$ represents an alkylene chain as defined in the description,
and A represents a NRCOR', NRCSR', CONRR', CSNRR', NRCONR'R" or NRCSNR'R" group.

15 Claims, No Drawings

OTHER PUBLICATIONS

Fanteck, et al., *Exp. Brain Res.,* 1995, 107, 321-325.
Rasmussen, et al., *Endocrinology,* 1999, 140, 1009-1012.
Armstrong, et al., *Medical Hypotheses,* 1991, 34, 300-309.
O'Brien, et al., *Clinical Endocrinology,* 1986, 24, 359-364.
Motilva, et al., *Current Pharmaceutical Design,* 2001, 7, 909-931.
Tamarkin, et al., *Science,* 1985, 227, 714-720.
Chemineau, et al., *Rec. Med. Vet.,* 1991, 167, 227-239.
Xu, et al., *Drug Development Research,* 1996, 39, 167-173.
Régrigny, et al., *Am. J. Physiol.,* 1998, 275, 139-144.
Stankov, et al., *Neuroscience,* 1993, 52, 459-468.
Leone, et al., *Cephalalgia,* 1996, 16, 494-496.
Brun, et al., *Cephalalgia,* 1995, 15, 136-139.
Ying, et al., *Eur. J. of Pharmacology,* 1993, 246, 89-96.
Laudon, et al., *Journal of Clinical Endocrinology and Metabolism,* 1996, 81, 1336-1342.
Lissoni, et al., *British Journal of Cancer,* 1996, 74, 1466-1468.
Mariusz, et al., *Neuropsychopharmacology,* 2003, 28, 694-703.
Overstreet, et al., *Neuroreport,* 1998, 9, 249-253.
Barden, et al., *Progress in Neuro-Psychopharmacology and Biological Psychiatry,* 2005, 29, 908-916.
Kopp, et al., *Neuropharmacology,* 2000, 39, 1865-1871.
Becker, et al., *Neuropharmacology,* 2004, 46, 1158-1167.
Tuma, et al., *European Neuropsychopharmacology,* 2005, 15, 545-555.
Zhdanova, et al., *J. Clin. Endocrinol. Metab.,* 2001, 86, 4727-4730.
Fischer, et al., *J. Clin. Endocrinol. Metab.,* 2003, 88, 5315-5320.
Lewy, et al., *Psychiatry Research,* 1998, 77, 57-61.
Danilenko, et al., *Neuropsychopharmacology,* 2005, 30, 1345-1352.

SUBSTITUTED BIPHENYL DERIVATIVES, METHOD FOR PREPARING SAME AND PHARMACEUTICAL COMPOSITIONS CONTAINING SAME

The present invention relates to new substituted biphenyl compounds, to a process for their preparation and to pharmaceutical compositions containing them.

There are known from the literature indolic biphenyl compounds that are useful as metalloprotease inhibitors (WO 96 15096) or specific ligands of 5HT-1B and 5HT-1D receptors (WO 95 01334).

Also, benzimidazolic biphenyl compounds are described in Patent Application EP 468 470 as angiotensin inhibitors.

In view of their novel structure, the compounds of the present invention are new and they exhibit pharmacological properties of great interest in relation to melatoninergic receptors.

In the last ten years, numerous studies have demonstrated the major role played by melatonin (N-acetyl-5-methoxytryptamine) in a large number of physiopathological phenomena and in the control of the circadian rhythm, but melatonin has a rather short half-life owing to the fact that it is rapidly metabolised. Great interest therefore lies in the possibility of making available to the clinician melatonin analogues that are metabolically more stable and have an agonist or antagonist character and of which the therapeutic effect may be expected to be superior to that of the hormone itself.

In addition to their beneficial action in respect of circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, for example anxiolytic and antipsychotic properties (Neuropharmacology of Pineal Secretions, 1990, 8 (3–4), pp. 264–272), and analgesic properties (Pharmacopsychiat., 1987, 20, pp. 222–223), and also for the treatment of Parkinson's disease (J. Neurosurg. 1985, 63, pp. 321–341) and Alzheimer's disease (Brain Research, 1990, 528, pp. 170–174). Such compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20 (4), pp. 443–446).

Those various effects are exerted via the intermediary of specific melatonin receptors. Molecular biology studies have demonstrated the existence of a number of receptor subtypes that are capable of binding that hormone (Trends Pharmacol. Sci., 1995, 16, p. 50; WO 97.04094). It has been possible for some of those receptors to be located and characterised for different species, including mammals. In order to be able to understand the physiological functions of those receptors better, to have specific ligands available is of great interest. Moreover such compounds, by interacting selectively with one or another of those receptors, may be excellent medicaments for the clinician in the treatment of pathologies associated with the melatoninergic system, some of which have been mentioned above.

In addition to being new, the compounds of the present invention exhibit a very strong affinity for melatonin receptors and/or a selectivity for one or another of the melatoninergic receptor sub-types.

More especially, the present invention relates to compounds of formula (I):

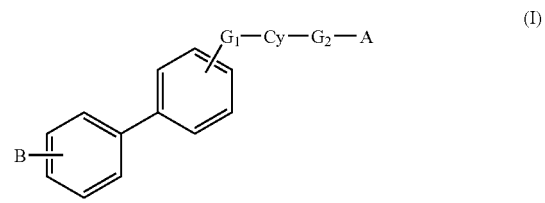

wherein:

B represents a hydrogen atom, a COOR group, a CONRR' group, or a linear or branched ($C_1$–$C_6$)alkyl group substituted by a COOR, CONRR' or OR group (wherein R and R', which may be identical or different, each represents a hydrogen atom, or a group linear or branched ($C_1$–$C_6$)alkyl, linear or branched ($C_2$–$C_6$)alkenyl, linear or branched ($C_2$–$C_6$)alkynyl, aryl, aryl-($C_1$–$C_6$)alkyl in which the alkyl moiety may be linear or branched, heteroaryl, heteroaryl-($C_1$–$C_6$)alkyl in which the alkyl moiety may be linear or branched, polyhalo-($C_1$–$C_6$)alkyl in which the alkyl moiety may be linear or branched, ($C_3$–$C_8$)cycloalkyl or ($C_3$–$C_8$)cycloalkyl-($C_1$–$C_6$)alkyl in which the alkyl moiety may be linear or branched, it being possible in addition for R and R' to form, together with the nitrogen atom carrying them, a morpholinyl, piperidyl, piperazinyl or pyrrolidinyl group), $G_1$ represents a —X'—$(CH_2)_n$—X—$(CH_2)_m$—X"— chain wherein X represents an oxygen or sulphur atom, or a $CH_2$ or NR group (wherein R is as defined hereinbefore), X' and X", which may be identical or different, each represents an oxygen or sulphur atom or an NR group (wherein R is as defined hereinbefore), n and m, which may be identical or different, each represents 0, 1, 2, 3, 4 or 5, it being understood that it is not possible to have two consecutive hetero atoms and that the chain so defined may contain one or more unsaturations, Cy represents a grouping of formula (II)

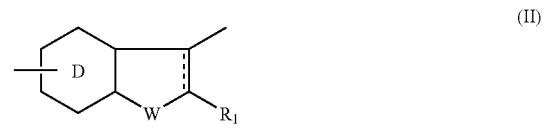

wherein D represents a phenyl or a pyridine, W represents an oxygen or sulphur atom, or a $CH_2$ or NR group (wherein R is as defined hereinbefore), $R_1$ represents a halogen atom or an R, OR or COOR group (wherein R is as defined hereinbefore) and the representation ----- denotes that the bond is single or double, it being understood that the valency of the atoms is respected, or a grouping of formula (III)

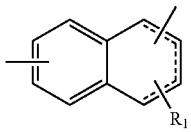

wherein $R_1$ and the representation ---- are as defined hereinbefore, $G_2$ represents a chain containing from 1 to 6 carbon atoms that is optionally substituted by one or more groups selected from R, OR, COR, COOR (wherein R is as defined hereinbefore) and halogen atoms, and A represents a NRCOR', NRCSR', CONRR', CSNRR', NRCONR'R" or NRCSNR'R" group (wherein R and R' are as defined hereinbefore and R" may have the same meanings as R and R'), wherein:

"aryl" is to be understood as meaning a phenyl or naphthyl group that is unsubstituted or substituted by one or more identical or different groups selected from R, OR, COR, COOR, NRR' (wherein R and R' are as defined hereinbefore), nitro, cyano and halogen atoms, "heteroaryl" is to be understood as meaning any mono- or bi-cyclic group having from 5 to 10 ring members and capable of containing from 1 to 3 hetero atoms selected from oxygen, sulphur and nitrogen, that group being unsubstituted or substituted by one or more identical or different groups selected from R, OR, COR, COOR, NRR' (wherein R and R' are as defined hereinbefore), nitro, cyano and halogen atoms, to their enantiomers and diastereoisomers and also to addition salts thereof with a pharmaceutically acceptable acid or base.

Among the pharmaceutically acceptable acids there may be mentioned by way of non-limiting example hydrochloric, hydrobromic, sulphuric, phosphoric, acetic, trifluoroacetic, lactic, pyruvic, malonic, succinic, glutaric, fumaric, tartaric, maleic, citric, ascorbic, methanesulphonic, camphoric acid etc.

Among the pharmaceutically acceptable bases there may be mentioned by way of non-limiting example sodium hydroxide, potassium hydroxide, triethylamine, tert-butylamine etc.

Preferred compounds of the invention are compounds of formula (I) wherein B represents:

a COOR group wherein R is preferably a hydrogen atom or a linear or branched ($C_1$–$C_6$)alkyl group, such as, for example, methyl, or a linear or branched ($C_1$–$C_6$)alkyl group substituted by a COOR or OR group, more especially COOH, alkyloxycarbonyl, OH or alkoxy.

The preferred $G_1$ group of the compounds of the invention is the group —O—$(CH_2)_p$—O— wherein p is an integer such that 0<p<6, such as, for example, —O—$(CH_2)_4$—O—.

The invention relates more especially to compounds of formula (I) wherein Cy represents a naphthalene, tetrahydronaphthalene, benzothiophene, benzofuran, indole, indene or azaindole group.

$G_2$ preferably represents a —$(CH_2)_2$— or —$(CH_2)_3$— group.

Preferred meanings for A are the groups NRCOR' and CONRR', more especially the groups NHCOR' and CONHR.

Even more especially, the invention relates to the following compounds of formula (I):

methyl 4'-[4-({8-[2-(acetylamino)ethyl]-2-naphthyl}oxy)butoxy]-[1,1'-biphenyl]-4-carboxylate, 4'-[4-({8-[2-(acetylamino)ethyl]-2-naphthyl}oxy)butoxy]-[1,1'-biphenyl]-4-carboxylic acid, N-{2-[7-(4-{[4'-(hydroxymethyl)-[1,1'-biphenyl]-4-yl]oxy}butoxy)-1-naphthyl]ethyl}-acetamide, N-(2-{7-[4-([1,1'-biphenyl]-4-yloxy)butoxy]-1-naphthyl}ethyl)acetamide, N-(2-{7-[4-([1,1'-biphenyl]-3-yloxy)butoxy]-1-naphthyl}ethyl)acetamide.

The enantiomers, diastereoisomers and also addition salts with a pharmaceutically acceptable acid or base of the preferred compounds of the invention form an integral part of the invention.

The present invention relates also to a process for the preparation of the compounds of formula (I), which process is characterised in that there is used as starting material a compound of formula:

$$\text{MeO-Cy-}G_2\text{-A} \qquad (IV)$$

wherein A, $G_2$ and Cy are as defined for formula (I), which is subjected to demethylation using conventional agents, such as HBr, $AlCl_3$, $AlBr_3$, $BBr_3$ or Lewis acid/nucleophile binary systems such as $AlCl_3/PhCH_2SH$ or $BBr_3/Me_2S$, for example, to obtain a compound of formula (V):

$$\text{HO-Cy-}G_2\text{-A} \qquad (V)$$

wherein A, $G_2$ and Cy are as defined hereinbefore, which is converted in conventional manner by the action of sodium N,N-dimethylthiocarbamate for example, to the corresponding thiol of formula (VI):

$$\text{HS-Cy-}G_2\text{-A} \qquad (VI)$$

wherein A, $G_2$ and Cy are as defined hereinbefore, or to the corresponding amine compound of formula (VII):

$$\text{RNH-Cy-}G_2\text{-A} \qquad (VII)$$

wherein A, $G_2$, Cy and R are as defined hereinbefore, the compounds of formula (V), (VI) and (VII) representing the compound of formula (VIII):

$$\text{HX''-Cy-}G_2\text{-A} \qquad (VIII)$$

wherein Cy, $G_2$, X" and A are as defined hereinbefore, which compound of formula (VIII) is condensed with a compound of formula (IX):

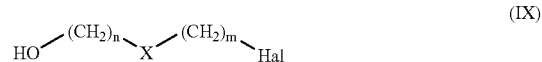

wherein Hal represents a bromine, chlorine or iodine atom, and X, n and m are as defined for formula (I), (it being understood that it is not possible to have two consecutive hetero atoms and that the chain so defined may contain one or more unsaturations), to yield a compound of formula (X):

$$\text{HO—}(CH_2)_n\text{—X—}(CH_2)_m\text{—X''-Cy-}G_2\text{-A} \qquad (X)$$

wherein A, $G_2$, Cy, X, X", n and m are as defined hereinbefore (it being understood that it is not possible to have two consecutive hetero atoms in the HO—$(CH_2)_n$—X—$(CH_2)_m$—X"— chain and that the chain so defined may contain one or more unsaturations),
the hydroxy function of which is converted in conventional manner into a leaving group, such as, for example, a mesylate, a tosylate, or a halogenated compound, to yield a compound of formula (X'):

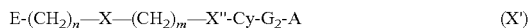
E-$(CH_2)_n$—X—$(CH_2)_m$—X"-Cy-$G_2$-A  (X')

wherein A, $G_2$, Cy, X, X", n and m are as defined hereinbefore and E represents a mesyl or tosyl group or a halogen atom,
which is reacted in basic medium with a compound of formula (XI):

B'-Ph-Ph-X'H  (XI)

wherein X' is as defined for formula (I), and B' may have the same meanings as B as defined for formula (I) with the exception of the groups COOH and alkyl substituted by a COOH group,
to yield a compound of formula (I/a), a particular case of the compounds of formula (I):

B'-Ph-Ph-$G_1$-Cy-$G_2$-A  (I/a)

wherein A, $G_2$, $G_1$, Cy and B' are as defined hereinbefore,
the compound of formula (I/a) being subjected, when B' represents a COOR$_1$' group or alkyl substituted by a COOR$_1$' group (wherein R$_1$' may have any of the meanings of R defined hereinbefore with the exception of a hydrogen atom), to hydrolysis to yield a compound of formula (I/b), a particular case of the compounds of formula (I):

B"-Ph-Ph-$G_1$-Cy-$G_2$-A  (I/b)

wherein A, $G_2$, $G_1$ and Cy are as defined hereinbefore, and B" represents a COOH group or alkyl substituted by a COOH group,
the totality of the compounds (I/a) and (I/b) constituting the compounds of formula (I) which may, if desired, be purified by a conventional purification technique, are optionally separated into their isomers according to a conventional separation technique and, if desired, are converted into addition salts with a pharmaceutically acceptable acid or base.

The compounds of formula (IV) are readily obtainable by the person skilled in the art according to methods described in the literature.

The compounds of the invention and pharmaceutical compositions containing them have proved to be useful in the treatment of disorders of the melatoninergic system.

A pharmacological study of the compounds of the invention has in fact demonstrated that they are non-toxic, have a high affinity for melatonin receptors and have substantial activity in respect of the central nervous system and the microcirculation, enabling it to be established that the products of the invention are useful in the treatment of stress, sleep disorders, anxiety, seasonal affective disorders, cardiovascular pathologies, pathologies of the digestive system, insomnia and fatigue due to jetlag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory losses, Alzheimer's disease, and in cerebral circulation disorders. In another field of activity, it appears that the products of the invention can be used in the treatment of sexual dysfunctions, that they have ovulation-inhibiting and immunomodulating properties and that they are capable of being used in the treatment of cancers.

The compounds will preferably be used in the treatment of seasonal affective disorders, sleep disorders, cardiovascular pathologies, insomnia and fatigue due to jetlag, appetite disorders and obesity.

For example, the compounds will be used in the treatment of seasonal affective disorders and sleep disorders.

The present invention relates also to pharmaceutical compositions comprising at least one compound of formula (I) on its own or in combination with one or more pharmaceutically acceptable excipients.

Amongst the pharmaceutical compositions according to the invention there may be mentioned more especially those which are suitable for oral, parenteral, nasal, per- or transcutaneous, rectal, perlingual, ocular or respiratory administration, especially tablets or dragées, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication or possibly associated treatments, and ranges from 0.01 mg to 1 g per 24 hours in one or more administrations.

The following Examples illustrate the invention but do not limit it in any way. The following Preparations result in compounds of the invention or in synthesis intermediates useful in the preparation of the invention.

Preparation 1:
N-[2-(7-Hydroxy-1-naphthyl)ethyl]acetamide

Under an inert atmosphere, 27.5 mmol of boron tribromide/dimethyl sulphide complex are dissolved in 100 ml of dichloromethane and stirred for 15 minutes at ambient temperature. A solution of 13.7 mmol of N-[2-(7-methoxy-1-naphthyl)ethyl]acetamide in 50 ml of dichloromethane is added, and the reaction mixture is heated at reflux for 30 hours. After cooling, the reaction mixture is cautiously hydrolysed and the dichloromethane is evaporated off. The mixture is then extracted with ethyl acetate and the combined organic phases are washed with an aqueous 1M potassium hydrogen carbonate solution. The organic phase is dried over magnesium sulphate and concentrated to yield the title compound. White solid.

Melting Point: 125–126° C.

By proceeding as in Preparation 1, using as starting material the appropriate substrate, Preparations 2 to 14 are obtained:

Preparation 2: N-[2-(5-Hydroxy-1-benzofuran-3-yl)ethyl] acetamide

Preparation 3: N-[2-(5-Hydroxy-1-benzofuran-3-yl)ethyl] cyclopropanecarboxamide

Preparation 4: N-[2-(5-Hydroxy-1-benzofuran-3-yl)ethyl]-2-furamide

Preparation 5: N-[2-(7-Hydroxy-1-naphthyl)ethyl]butanamide

Preparation 6: N-[2-(5-Hydroxy-1-benzothien-3-yl)ethyl] acetamide

Preparation 7: N-[2-(5-Hydroxy-1H-pyrrolo[2,3-b]pyrid-3-yl)ethyl]cyclopropane-carboxamide Preparation 8: N-[2-(5-Hydroxy-1H-indol-3-yl)ethyl]acetamide Preparation 9: N-[2-(5-Hydroxy-1H-pyrrolo[2,3-b]pyrid-3-yl)ethyl]acetamide Preparation 10: N-[2-(7-Hydroxy-1-naphthyl)ethyl]cyclobutanecarboxamide Preparation 11: 2,2,2-Trifluoro-N-[2-(7-hydroxy-1-naphthyl)ethyl]acetamide Preparation 12: N-[2-(7-Hydroxy-1-naphthyl)ethyl]-2-furamide Preparation 13: N-[2-(2-Benzyl-5-hydroxy-1H-pyrrolo[2,3-b]pyrid-3-yl)ethyl]-acetamide Preparation 14: N-[2-(5-Hydroxy-1H-inden-3-yl)ethyl]pentanamide Preparation 15: N-[2-(5-Mercapto-1-benzofuran-3-yl)ethyl]acetamide The product obtained in Preparation 2 (9 mmol) is added, with stirring, to a solution of potassium hydroxide (10 mmol) dissolved in 15 ml of water and 16 ml of tetrahydrofuran. The solution is cooled using an ice/salt bath, and dimethylthiocarbamoyl chloride (9 mmol) dissolved in tetrahydrofuran (15 ml) is added dropwise with stirring. After stirring for half an hour while keeping cold, the reaction mixture is extracted with chloroform. The organic phases are combined, dried over magnesium sulphate, filtered and then concentrated under reduced pressure. The residue is taken up in diphenyl ether (10 ml) and heated at reflux for one hour under a nitrogen atmosphere. The diphenyl ether is evaporated off under reduced pressure until a solution of approximately 2 ml is obtained. The 2 ml of distillate are cautiously poured, while still hot, into 50 ml of hexane to yield, after cooling, a solid isolated by filtration. The solid so obtained is added to a solution of potassium hydroxide (380 mg) dissolved in a water/methanol (1 ml/10 ml) mixture. The solution is heated at reflux for 12 hours and then cooled and concentrated under reduced pressure. The residue is taken up in 20 ml of chloroform and extracted 3 times with water. The organic phase is dried over magnesium sulphate, filtered and concentrated under reduced pressure. The residue is chromatographed on silica gel to yield the title product.

Preparation 16:
N-[2-(5-Amino-1-benzofuran-3-yl)ethyl]acetamide

Step A: N-[2-(5-Bromo-1-benzofuran-3-yl)ethyl]acetamide

Triphenylphosphine (10 mmol) and acetonitrile (70 ml) are poured into a 150 ml three-necked flask equipped with a dropping funnel, a condenser on top of which is mounted a tube filled with calcium chloride, and a mechanical stirrer. The solution is cooled using an ice-bath while maintaining stirring, and bromine (10 mmol) is added. When the addition is complete, the ice-bath is removed and then the product obtained in Preparation 2 (8 mmol) is added. The reaction mixture is stirred at 60–70° C. until the starting material has disappeared. At the end of the reaction, the mixture is filtered, and then the filtrate is concentrated under reduced pressure. The residue is taken up in ethyl acetate, washed with water and then with a saturated potassium hydrogen carbonate solution, and once again with water, and then dried over magnesium sulphate and concentrated under reduced pressure. The residue is filtered over silica gel to yield the title product.

Step B: N-[2-(5-Iodo-1-benzofuran-3-yl)ethyl]acetamide

A mixture of the product obtained in Step A (2 mmol), potassium iodide (30 mmol) and copper(I) iodide (10 mmol) in hexamethylphosphoramide (6 ml) is heated at 150–160° C. with stirring, under a nitrogen atmosphere, until a 90% conversion rate has been reached. Dilute hydrochloric acid is then added, followed by ether, and the mixture is then filtered to remove the insoluble copper(I) salts. The organic phase is separated off, washed with a solution of sodium sulphite and with water, dried over magnesium sulphate and evaporated to yield a residue which is chromatographed on silica gel to yield the title product.

Step C: N-[2-(5-Vinyl-1-benzofuran-3-yl)ethyl]acetamide 15 mmol of the product obtained in Step B, 16 mmol of vinyltributyltin and 0.43 mmol of tetrakis(triphenylphosphine)palladium are heated for 3 hours at 110° C., with stirring, in 30 ml of N-methylpyrrolidinone. After removal of the solvent by evaporation, the residue is taken up in 20 ml of dichloromethane and treated with an aqueous 10% potassium fluoride solution. Extraction, concentration under reduced pressure and chromatography on silica gel yield the pure title product.

Step D: N-[2-(5-Formyl-1-benzofuran-3-yl)ethyl]acetamide 1.10 g of osmium tetroxide in 2-methyl-2-propanol and then 8.70 g of sodium periodate are added at ambient temperature to a solution of 10 mmol of the product obtained in Step C in a mixture of 50 ml of dioxane and 25 ml of water. After stirring overnight at ambient temperature, the suspension is filtered and the filtrate is concentrated under reduced pressure. The resulting residue is taken up in dichloromethane. The organic phase is washed with water, dried and evaporated. The residue is purified by chromatography on silica gel to yield the title product.

Step E: 3-[2-(Acetylamino)ethyl]-1-benzofuran-5-carboxylic acid 2.7 g of potassium permanganate in 50 ml of an acetone/water mixture (50/50) are added at ambient temperature to a solution of 6.88 mmol of the product obtained in Step D in 30 ml of acetone. The solution is stirred for 2 hours at ambient temperature and then filtered. The filtrate is concentrated under reduced pressure and chromatographed on silica gel to yield the title product.

Step F: 3-[2-(Acetylamino)ethyl]-1-benzofuran-5-carboxylic acid chloride 5 mmol of the product obtained in Step E are dissolved in 40 ml of thionyl chloride. After stirring under an inert atmosphere for 1 hour, the thionyl chloride is removed by evaporation under reduced pressure to yield the title product.

Step G: N-[2-(5-Amino-1-benzofuran-3-yl)ethyl]acetamide

A solution of the product obtained in Step F (20 mmol) in dichloromethane (30 ml) containing tetrabutylammonium bromide (20 mg) is cooled in an ice-bath. After the addition of sodium azide (25 mmol) dissolved in 5 ml of water, the solution is stirred vigorously at 0° C. for 2 hours. The organic phase is separated off, washed with water (2×5 ml) and dried over magnesium sulphate. After filtration, trifluoroacetic acid (30 mmol) is added and the solution is stirred under reflux for 60 hours. After cooling, the organic phase is washed with a saturated sodium hydrogen carbonate solution (2×5 ml) and concentrated under reduced pressure. The residue is then taken up in methanol (20 ml), and water (80 ml) and then potassium carbonate (30 mmol) are added. After stirring at ambient temperature for 20 hours, the reaction mixture is concentrated under reduced pressure to a volume of about 60 ml, and is then extracted 3 times with ether (3×50 ml). After drying over sodium sulphate, the organic phase is filtered and then evaporated under reduced pressure. The residue is chromatographed on silica gel to yield the title product.

Preparation 17: N-[2-(5-Amino-1-benzofuran-3-yl)ethyl]-2-furamide

The procedure is as in Preparation 16 starting from the compound obtained in Preparation 4.

Preparation 18: N-[2-(5-Hydroxy-1-methyl-1H-pyrrolo[2,3-b]pyrid-3-yl)ethyl]-acetamide The procedure is as in Preparation 1.

Preparation 19: N-[2-(7-Hydroxy-1,2,3,4-tetrahydro-1-naphthyl)ethyl]acetamide

The procedure is as in Preparation 1.

Preparation 20: N-[2-(5-Hydroxy-1-methyl-1H-pyrrolo[3,2-b]pyrid-3-yl)ethyl]-acetamide The procedure is as in Preparation 1.

EXAMPLE 1

Methyl 4'-[2-({8-[2-(acetylamino)ethyl]-2-naphthyl}oxy)ethoxy]-[1,1'-biphenyl]-4-carboxylate Step A: N-{2-[7-(2-Bromoethoxy)naphth-1-yl]ethyl}acetamide The compound obtained in Preparation 1 (0.009 mol) is dissolved in 20 ml of a mixture of dimethyl sulphoxide (6 ml) and butanone (14 ml). 0.027 mol of potassium carbonate and 0.036 mol of dibromoethane are added, and the mixture is heated at reflux for 48 hours. The reaction mixture is then cooled and poured into water. The aqueous phase is extracted with $Et_2O$, and then the organic phase is washed with water until the washing waters are neutral, and subsequently dried over magnesium sulphate and evaporated under reduced pressure. The resulting residue is purified by chromatography on silica gel (eluant:acetone/cyclohexane (2/8)) and recrystallised. White solid.

Melting Point: 110–111° C.

| Elemental microanalysis: | | | |
| --- | --- | --- | --- |
| % | C | H | N |
| Calculated: | 57.15 | 5.40 | 4.17 |
| Found: | 57.28 | 5.38 | 3.91 |

Step B: Methyl 4'-[2-({8-[2-(acetylamino)ethyl]-2-naphthyl}oxy)ethoxy]-[1,1'-biphenyl]-4-carboxylate In a 100 ml round-bottomed flask, 0.003 mol of methyl 4'-hydroxy[1,1'-biphenyl]-4-carboxylate and 0.003 mol of the compound obtained in Step A are dissolved in a mixture of 3 ml of dimethyl sulphoxide and 20 ml of butanone. 0.009 mol of potassium carbonate and one potassium iodide crystal are added and then the mixture is heated at reflux for 12 hours. The reaction mixture is then cooled and poured into 100 ml of water. The precipitate that forms is suctioned off and recrystallised to yield the title product.

EXAMPLE 2

4'-[2-({8-[2-(Acetylamino)ethyl]-2-naphthyl}oxy)ethoxy]-[1,1'-biphenyl]-4-carboxylic acid In a 100 ml round-bottomed flask, 19 mmol of the compound obtained in Example 1 are suspended in 25 ml of THF, and then 15 ml of methanol, 15 ml of water and 38 mmol of sodium hydroxide are added. The reaction mixture is maintained at ambient temperature with stirring for 10 hours. The solution is subsequently concentrated, poured into water and then acidified with 12M HCl. The precipitate obtained is filtered off, washed with water and recrystallised to yield the title product.

EXAMPLE 3

Methyl 4'-[2-({3-[2-(acetylamino)ethyl]-1-benzofuran-5-yl}oxy)ethoxy]-[1,1'-biphenyl]-4-carboxylate The procedure is as in Example 1, with the replacement in Step A of the compound obtained in Preparation 1 by the compound obtained in Preparation 2.

EXAMPLE 4

Methyl 4'-{2-[(3-{2-[(cyclopropylcarbonyl)amino]ethyl}-1-benzofuran-5-yl)oxy]ethoxy}-[1,1'-biphenyl]-4-carboxylate The procedure is as in Example 1, with the replacement in Step A of the compound obtained in Preparation 1 by the compound obtained in Preparation 3.

EXAMPLE 5

Methyl 4'-[2-({3-[2-(2-furoylamino)ethyl]-1-benzofuran-5-yl}oxy)ethoxy]-[1,1'-biphenyl]-4-carboxylate The procedure is as in Example 1, with the replacement in Step A of the compound obtained in Preparation 1 by the compound obtained in Preparation 4.

EXAMPLE 6

Methyl 4'-[2-({3-[2-(acetylamino)ethyl]-1-benzofuran-5-yl}amino)-ethoxy]-[1,1'-biphenyl]-4-carboxylate The procedure is as in Example 1, with the replacement in Step A of the compound obtained in Preparation 1 by the compound obtained in Preparation 16.

EXAMPLE 7

Methyl 4'-[2-({8-[2-(butyrylamino)ethyl]-2-naphthyl}oxy)ethoxy-[1,1'-biphenyl]-4-carboxylate The procedure is as in Example 1, with the replacement in Step A of the compound obtained in Preparation 1 by the compound obtained in Preparation 5.

EXAMPLE 8

Methyl 4'-[2-({3-[2-(acetylamino)ethyl]-1-benzothien-5-yl}oxy)ethoxy]-[1,1'-biphenyl]-4-carboxylate The procedure is as in Example 1, with the replacement in Step A of the compound obtained in Preparation 1 by the compound obtained in Preparation 6.

EXAMPLE 9

Methyl 4'-{2-[(3-{2-[(cyclopropylcarbonyl)amino]ethyl}-1H-pyrrolo-[2,3-b]pyrid-5-yl)oxy]ethoxy}-[1,1'-biphenyl]-4-carboxylate The procedure is as in Example 1, with the replacement in Step A of the product obtained in Preparation 1 by the compound obtained in Preparation 7.

EXAMPLE 10

N-{2-[7-(2-{[4'-(Hydroxymethyl)-[1,1'-biphenyl]-4-yl]oxy}ethoxy)-1-naphthyl]ethyl}acetamide The procedure is as in Example 1, with the replacement in Step B of methyl 4'-hydroxy[1,1'-biphenyl]-4-carboxylate by 4'-(hydroxymethyl)-[1,1'-biphenyl]-4-ol.

EXAMPLE 11

Methyl 4'-[2-({3-[2-(acetylamino)ethyl]-1H-indol-5-yl}oxy)ethoxy]-[1,1'-biphenyl]-4-carboxylate The procedure is as in Example 1, with the replacement in Step A of the compound obtained in Preparation 1 by the compound obtained in Preparation 8.

EXAMPLE 12

4'-[2-({3-[2-(Acetylamino)ethyl]-1H-indol-5-yl}oxy)ethoxy]-[1,1'-biphenyl]-4-carboxylic acid The procedure is as in Example 2, starting from the compound obtained in Example 11.

EXAMPLE 13

Methyl 4'-[3-({8-[2-(acetylamino)ethyl]-2-naphthyl}oxy)propoxy]-[1,1'-biphenyl]-4-carboxylate Step A: N-{2-[7-(3-Hydroxypropyloxy)naphth-1-yl]ethyl}acetamide In a 100 ml round-bottomed flask, 0.022 mol of the compound obtained in Preparation 1 is dissolved in 30 ml of dimethylformamide. 0.066 mol of potassium carbonate and 0.033 mol of 3-bromopropan-1-ol are added, and then the mixture is heated at 80° C. for 4 hours. The reaction mixture is cooled and poured into 100 ml of a 1M HCl solution. The aqueous phase is extracted 3 times with $Et_2O$ and then the organic phase is dried over $MgSO_4$ and evaporated under reduced pressure. The title product is obtained by recrystallisation. White solid.

Melting Point: 141–142° C.

Step B: 3-({8-[2-(Acetylamino)ethyl]-2-naphthyl}oxy)propyl methanesulphonate

In a 250 ml round-bottomed flask, the alcohol obtained in Step A is dissolved in 50 ml of dichloromethane, and 0.012 mol of triethylamine is added. The mixture is cooled in an ice/salt bath at −10° C., and then 0.012 mol of mesyl chloride is added dropwise with magnetic stirring. The reaction mixture is stirred at ambient temperature for 4 hours. 100 ml of water are then added, followed by extraction with $CH_2Cl_2$. The organic phase is washed with water, dried over $MgSO_4$ and evaporated under reduced pressure. The resulting oil is purified by chromatography on silica gel (eluant:acetone/cyclohexane (2/8)).

Step C: Methyl 4'-[3-({8-[2-(acetylamino)ethyl]-2-naphthyl}oxy)propoxy]-[1,1'-biphenyl]-4-carboxylate In a 100 ml round-bottomed flask containing 30 ml of methanol, 0.06 g of sodium is added in small portions. When the sodium has been completely used up, 0.0033 mol of methyl 4'-hydroxy[1,1'-biphenyl]-4-carboxylate is added and the mixture is stirred for 20 minutes. The methanol is removed by evaporation under reduced pressure, the residue is taken up in 15 ml of DMF, and then 0.0027 mol of the compound obtained in Step B is added. The reaction mixture is then heated at reflux for 12 hours and subsequently cooled and poured into 100 ml of water and 10 ml of 3M HCl. After extraction with ethyl acetate, the organic phase is washed with a 10% sodium hydroxide solution and then with water. After drying over $MgSO_4$ and removal of the solvent by evaporation under reduced pressure, the title compound is purified by chromatography on silica gel.

EXAMPLE 14

Methyl 4'-{3-[(8-{2-[(cyclobutylcarbonyl)amino]ethyl}-2-naphthyl)oxy]-propoxy}-[1,1'-biphenyl]4-carboxylate The procedure is as in Example 13, starting from the compound obtained in Preparation 10.

EXAMPLE 15

Methyl 4'-[3-({3-[2-(2-furoylamino)ethyl]-1-benzofuran-5-yl}amino)-propoxy]-[1,1'-biphenyl]-4-carboxylate The procedure is as in Example 13, starting from the compound obtained in Preparation 17.

EXAMPLE 16

4'-[3-({3-[2-(2-Furoylamino)ethyl]-1-benzofuran-5-yl}aminopropoxy]-1,1'-biphenyl]-4-carboxylic acid The procedure is as in Example 2, starting from the compound obtained in Example 15.

EXAMPLE 17

Methyl 4'-{3-[(8-{2-[(trifluoroacetyl)amino]ethyl}-2-naphthyl)oxy]-propoxy}-[1,1'-biphenyl]-4-carboxylate The procedure is as in Example 13, with the replacement of the compound of Preparation 1 by the compound of Preparation 11.

EXAMPLE 18

4'-{3-[(8-{2-[(Trifluoroacetyl)amino]ethyl}-2-naphthyl)oxy]propoxy}-[1,1'-biphenyl]-4-carboxylic acid The procedure is as in Example 2, starting from the compound obtained in Example 17.

EXAMPLE 19

Methyl 4'-[4-({8-[2-(acetylamino)ethyl]-2-naphthyl}oxy)butoxy]-[1,1'-biphenyl]-4-carboxylate Step A: N-{2-[7-(4-Bromobutoxy)-1-naphthyl]ethyl}acetamide The procedure is as in Step A of Example 1, with the replacement of dibromoethane by 1,4-dibromobutane.

Step B: Methyl 4'-[4-({8-[2-(acetylamino)ethyl]-2-naphthyl}oxy)butoxy-]-[1,1'-biphenyl]-4-carboxylate The procedure is as in Step B of Example 1.
White solid.
Melting Point: 166–168° C.

| Elemental microanalysis: | | | |
|---|---|---|---|
| % | C | H | N |
| Calculated: | 74.61 | 6.45 | 2.72 |
| Found: | 74.62 | 6.48 | 2.81 |

EXAMPLE 20

4'-[4-({8-[2-(Acetylamino)ethyl]-2-naphthyl}oxy)butoxy]-[1,1'-biphenyl]-4-carboxylic acid The procedure is as in Example 2, starting from the compound obtained in Example 19.
White solid.
Melting Point: 223–225° C.

| Elemental microanalysis | | | |
|---|---|---|---|
| % | C | H | N |
| Calculated: | 70.83 | 5.94 | 2.66 |
| Found: | 71.16 | 6.05 | 2.69 |

EXAMPLE 21

N-{2-[7-(4-{[4'-(Hydroxymethyl)-[1,1'-biphenyl]-4-yl]oxy}butoxy)-1-naphthyl]ethyl}acetamide The procedure is as in Example 19, with the replacement in Step B of methyl 4'-hydroxy[1,1'-biphenyl]-4-carboxylate by 4'-(hydroxymethyl)-[1,1'-biphenyl]-4-ol.
Beige solid.
Melting Point: 172–173° C.

| Elemental microanalysis: | | | |
|---|---|---|---|
| % | C | H | N |
| Calculated: | 76.99 | 6.88 | 2.90 |
| Found: | 76.74 | 6.70 | 3.12 |

EXAMPLE 22

N-(2-{7-[4-([1,1'-Biphenyl]-4-yloxy)butoxy]-1-naphthyl}ethyl)-acetamide

The procedure is as in Example 19, with the replacement in Step B of methyl 4'-hydroxy[1,1'-biphenyl]-4-carboxylate by (1,1'-biphenyl)-4-ol.
White solid.
Melting Point: 138–140° C.

| Elemental microanalysis: | | | |
|---|---|---|---|
| % | C | H | N |
| Calculated: | 79.44 | 6.89 | 3.10 |
| Found: | 79.19 | 6.93 | 3.24 |

EXAMPLE 23

N-(2-{7-[4-([1,1'-Biphenyl]-3-yloxy)butoxy]-1-naphthyl}ethyl)-acetamide

The procedure is as in Example 19, with the replacement in Step B of methyl 4'-hydroxy[1,1'-biphenyl]-4-carboxylate by (1,1'-biphenyl)-3-ol.
White solid.
Melting Point: 111–112° C.

| Elemental microanalysis: | | | |
|---|---|---|---|
| % | C | H | N |
| Calculated: | 79.44 | 6.89 | 3.10 |
| Found: | 79.23 | 6.79 | 3.21 |

EXAMPLE 24

Methyl 4'-[4-({3-[2-(acetylamino)ethyl]-1-benzofuran-5-yl}oxy)-butoxy]-[1,1'-biphenyl]-4-carboxylate The procedure is as in Example 19, starting from the compound obtained in Preparation 2.

EXAMPLE 25

Methyl 4'-[4-({3-[2-(acetylamino)ethyl]-1-benzothien-5-yl}oxy)-butoxy]-[1,1'-biphenyl]-4-carboxylate The procedure is as in Example 19, starting from the compound obtained in Preparation 6.

EXAMPLE 26

Methyl 4'-[4-({3-[2-(acetylamino)ethyl]-1H-pyrrolo[2,3-b]pyrid-5-yl}-oxy)butoxy]-[1,1'-biphenyl]-4-carboxylate The procedure is as in Example 19, starting from the compound obtained in Preparation 9.

EXAMPLE 27

4'-[4-({3-[2-(Acetylamino)ethyl]-1-benzofuran-5-yl}oxy)butoxy]-[1,1'-biphenyl]-4-carboxylic acid The procedure is as in Example 2, starting from the compound obtained in Example 24.

EXAMPLE 28

4'-[4-({3-[2-(Acetylamino)ethyl]-1-benzothien-5-yl}oxy)butoxy[1,1'-biphenyl]-4-carboxylic acid The procedure is as in Example 2, starting from the compound obtained in Example 25.

EXAMPLE 29

4'-[4-({3-[2-(Acetylamino)ethyl]-1H-pyrrolo[2,3-b]pyrid-5-yl}oxy)-butoxy]-[1,1'-biphenyl]-4-carboxylic acid The procedure is as in Example 2, starting from the compound obtained in Example 26.

EXAMPLE 30

Methyl 4'-[4-({3-[2-(acetylamino)ethyl]-2-benzyl-1H-pyrrolo[2,3-b]pyrid-5-yl}oxy)butoxy]-[1,1'-biphenyl]-4-carboxylate The procedure is as in Example 19, starting from the compound obtained in Preparation 13.

EXAMPLE 31

Methyl 4'-[4-({8-[2-(2-furoylamino)ethyl]-2-naphthyl}oxy)butoxy]-[1,1'-biphenyl]-4-carboxylate The procedure is as in Example 19, starting from the compound obtained in Preparation 12.

EXAMPLE 32

Methyl 4'-[4-({3-[2-(pentanoylamino)ethyl]-1H-inden-5-yl}oxy)-butoxy]-[1,1'-biphenyl]-4-carboxylate The procedure is as in Example 19, starting from the compound obtained in Preparation 14.

EXAMPLE 33

Methyl 4'-[4-({3-[2-(acetylamino)ethyl]-1-benzofuran-5-yl}thio)-butoxy]-[1,1'-biphenyl]-4-carboxylate The procedure is as in Example 19, starting from the compound obtained in Preparation 15.

EXAMPLE 34

Methyl 4'-[4-({3-[2-(acetylamino)ethyl]-1-methyl-1H-pyrrolo[2,3-b]pyrid-5-yl}oxy)butoxy]-[1,1'-biphenyl]-4-carboxylate The procedure is as in Example 19, starting from the compound obtained in Preparation 18.

EXAMPLE 35

Methyl 3'-[4-({8-[2-(acetylamino)ethyl]-5,6,7,8-tetrahydro-2-naphthyl}oxy)butoxy]-[1,1'-biphenyl]-3-carboxylate The procedure is as in Example 19, starting from the compound obtained in Preparation 19.

EXAMPLE 36

3'-[4-({8-[2-(Acetylamino)ethyl]-5,6,7,8-tetrahydro-2-naphthyl}-oxy)butoxy]-[1,1'-biphenyl]-3-carboxylic acid The procedure is as in Example 2, starting from the compound obtained in Example 35.

EXAMPLE 37

Ethyl 4'-[4-({3-[2-(acetylamino)ethyl]-1-methyl-1H-pyrrolo[3,2-b]pyrid-5-yl}oxy)butoxy]-[1,1'-biphenyl]-4-carboxylate The procedure is as in Example 19, starting from the compound obtained in Preparation 20 and ethyl 4'-hydroxy [1,1'-biphenyl]-4-carboxylate.

Melting Point: 145–146° C.

| Elemental microanalysis: | | | |
|---|---|---|---|
| % | C | H | N |
| Calculated: | 70.30 | 6.66 | 7.93 |
| Found | 69.84 | 6.67 | 7.94 |

Pharmacological Study

EXAMPLE A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (the dose that causes the death of 50% of the animals) was evaluated and demonstrated the low toxicity of the compounds of the invention.

EXAMPLE B

Melatonin Receptor Binding Study on *Pars tuberalis* Cells of Sheep

Melatonin receptor binding studies of the compounds of the invention were carried out according to conventional techniques on *Pars tuberalis* cells of sheep. The *Pars tuberalis* of the adenohypophysis is in fact characterised in mammals by a high density of melatonin receptors (Journal of Neuroendocrinology, 1, pp. 1–4, 1989).

Protocol

1) Sheep *Pars tuberalis* membranes are prepared and used as target tissue in saturation experiments to determine the binding capacities and affinities for 2-[$^{125}$I]-iodomelatonin.
2) Sheep *Pars tuberalis* membranes are used as target tissue in competitive binding experiments using the various test compounds in comparison with melatonin.

Each experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

EXAMPLE C

Melatonin $MT_1$ and $MT_2$ Receptor Binding Study

The $MT_1$, or $MT_2$ receptor binding experiments are carried out using 2-[$^{125}$I]-iodomelatonin as reference radioligand. The radioactivity retained is determined using a liquid scintillation counter.

Competitive binding experiments are then carried out in triplicate using the various test compounds. A range of different concentrations is tested for each compound. The results enable the binding affinities of the compounds tested ($IC_{50}$) to be determined.

Thus, the $IC_{50}$ values found for the compounds of the invention show binding for one or other of the $MT_1$ and $MT_2$ receptor sub-types, those values being $\leq 10$ μM.

EXAMPLE D

Action of the Compounds of the Invention on the Circadian Rhythms of Locomotive Activity of the Rat The involvement of melatonin in influencing the majority of physiological, biochemical and behavioural circadian rhythms by day/night alternation has made it possible to establish a pharmacological model for research into melatoninergic ligands.

The effects of the compounds are tested in relation to numerous parameters and, in particular, in relation to the circadian rhythms of locomotive activity, which are a reliable indicator of the activity of the endogenous circadian clock.

In this study, the effects of such compounds on a particular experimental model, namely the rat placed in temporal isolation (permanent darkness) are evaluated.

Experimental Protocol

One-month-old male rats are subjected, as soon as they arrive at the laboratory, to a light cycle of 12 hours of light per 24 hours (LD 12:12).

After 2 to 3 weeks' adaptation, they are placed in cages fitted with a wheel connected to a recording system in order to detect the phases of locomotive activity and thus monitor the nychthemeral (LD) or circadian (DD) rhythms.

As soon as the rhythms recorded show a stable pattern in the light cycle LD 12:12, the rats are placed in permanent darkness (DD).

Two to three weeks later, when the free course (rhythm reflecting that of the endogenous clock) is clearly established, the rats are given a daily administration of the compound to be tested.

The observations are made by means of visualisation of the rhythms of activity:

influence of the light rhythm on the rhythms of activity, disappearance of the influence on the rhythms in permanent darkness, influence by the daily administration of the compound; transitory or durable effect.

A software package makes it possible:

to measure the duration and intensity of the activity, the period of the rhythm of the animals during free course and during treatment, optionally to demonstrate by spectral analysis the existence of circadian and non-circadian (for example ultradian) components.

Results

The compounds of the invention clearly appear to have a powerful action on the circadian rhythm via the melatoninergic system.

EXAMPLE E

Light/Dark Cage Test

The compounds of the invention are tested on a behavioural model, the light/dark cage test, which enables the anxiolytic activity of the compounds to be revealed.

The equipment comprises two polyvinyl boxes covered with Plexiglas. One of the boxes is in darkness. A lamp is placed above the other box, yielding a light intensity of approximately 4000 lux at the centre of the box. An opaque plastic tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

After administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE F

Activity of the Compounds of the Invention on the Caudal Artery of the Rat

The compounds of the invention were tested in vitro on the caudal artery of the rat. Melatoninergic receptors are present in those vessels, thus providing a relevant pharmacological model for studying melatoninergic ligand activity. The stimulation of the receptors can induce either vasoconstriction or dilation depending upon the arterial segment studied.

Protocol

One-month-old rats are habituated to a light/darkness cycle of 12 h/12 h for a period of 2 to 3 weeks.

After sacrifice, the caudal artery is isolated and maintained in a highly oxygenated medium. The arteries are then cannulated at both ends, suspended vertically in an organ chamber in a suitable medium and perfused via their proximal end. The pressure changes in the perfusion flow enable evaluation of the vasoconstrictive or vasodilatory effect of the compounds.

The activity of the compounds is evaluated on segments that have been pre-contracted by phenylephrine (1 μM). A concentration/response curve is determined non-cumulatively by the addition of a concentration of the test compound to the pre-contracted segment. When the effect observed reaches equilibrium, the medium is changed and the preparation is left for 20 minutes before the addition of the same concentration of phenylephrine and a further concentration of the test compound.

Results

The compounds of the invention significantly modify the diameter of caudal arteries pre-constricted by phenylephrine.

EXAMPLE G

Pharmaceutical Composition: Tablets 1000 tablets each containing a dose of 5 mg of 4'-[4-({8-[2-(acetylamino)ethyl]-2-naphthyl}oxy)butoxy]-[1,1'-biphenyl]-4-carboxylic acid (Example 20) . . . 5 g
Wheat starch . . . 20 g
Maize starch . . . 20 g
Lactose . . . 30 g
Magnesium stearate . . . 2 g
Silica . . . 1 g
Hydroxypropyl cellulose . . . 2 g

What is claimed is:

1. A compound selected from those of formula (I):

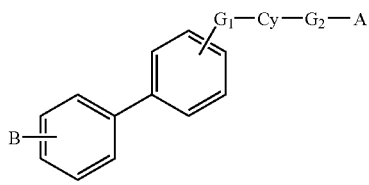

wherein:
B represents a hydrogen atom, a COOR, a CONRR', or a linear or branched ($C_1$–$C_6$)alkyl substituted by a COOR, CONRR', or OR wherein R and R', which may be identical or different, each represents hydrogen, or linear or branched ($C_1$–$C_6$)alkyl, linear or branched ($C_2$–$C_6$)alkenyl, linear or branched ($C_2$–$C_6$)alkynyl, aryl, aryl-($C_1$–$C_6$)alkyl in which the alkyl moiety may be linear or branched, heteroaryl, heteroaryl-($C_1$–$C_6$)alkyl in which the alkyl moiety may be linear or branched, polyhalo-($C_1$–$C_6$)alkyl in which the alkyl moiety may be linear or branched, ($C_3$–$C_8$)cycloalkyl or ($C_3$–$C_8$)cycloalkyl-($C_1$–$C_6$)alkyl in which the alkyl moiety may be linear or branched, it being possible in addition for R and R' to form, together with the nitrogen atom carrying them, a morpholinyl, piperidyl, piperazinyl, or pyrrolidinyl, $G_1$ represents a —X'—($CH_2$)$_n$—X—($CH_2$)$_m$—X"— chain wherein
X represents $CH_2$,
X' and X", which may be identical or different, each represents an oxygen or sulphur,
n and m, which may be identical or different, each represents 0, 1, 2, 3, 4 or 5, it being understood that it is not possible to have two consecutive hetero atoms in the chain and that the chain so defined may contain one or more unsaturations, Cy represents a grouping of formula (III)

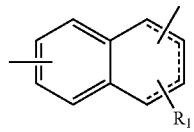

wherein $R_1$ represents a halogen, R, OR, or COOR, wherein R is as defined hereinbefore and the representation ----- denotes that the bond single is or double, it being understood that the valency of the atoms is respected, $G_2$ represents a 1 to 6 carbon atom chain containing that is optionally substituted by one or more groups selected from R, OR, COR, COOR wherein R is as defined hereinbefore, and halogen, and A represents a NRCOR', NRCSR', CONRR', CSNRR', NRCONR'R", or NRCSNR'R", wherein R and R' are as defined hereinbefore and R" may have the same meanings as R and R', it being understood that:
"aryl" represents phenyl or naphthyl that is unsubstituted or substituted by one or more identical or different groups selected from R, OR, COR, COOR, NRR', wherein R and R' are as defined hereinbefore, nitro, cyano and halogen, and "heteroaryl" is to be understood as meaning represents any mono- or bi-cyclic group having from 5 to 10 ring members and capable of containing from 1 to 3 hetero atoms selected from oxygen, sulphur, and nitrogen, that group being unsubstituted or substituted by one or more identical or different groups selected from R, OR, COR, COOR, NRR', wherein R and R' are as defined hereinbefore, nitro, cyano and halogen, its enantiomers and diastereoisomers, and also addition salts thereof with a pharmaceutically acceptable acid or base.

2. A compound of claim 1 wherein B represents COOR.
3. A compound of claim 2 wherein R represents hydrogen.
4. A compound of claim 2 wherein R represents linear or branched ($C_1$–$C_6$) alkyl.
5. A compound of claim 1 wherein B represents linear or branched ($C_1$–$C_6$)alkyl substituted by COOR.
6. A compound of claim 1 wherein B represents linear or branched ($C_1$–$C_6$)alkyl substituted by OR.
7. A compound of claim 1 wherein $G_1$ represents —O—($CH_2$)$_p$—O— in which p is an integer such that 0<p<6.
8. A compound of claim 1 wherein Cy represents naphthalene.
9. A compound of claim 1 wherein A represents NHCOR.
10. A compound of claim 1 which is selected from methyl 4'-[4-({8-[2-(acetylamino)ethyl]-2-naphthyl}oxy)butoxy]-

[1,1'-biphenyl]-4-carboxylate, and addition salts thereof with a pharmaceutically-acceptable acid or base.

11. A compound of claim 1 which is selected from 4'-[4-({8-[2-(acetylamino)ethyl]-2-naphthyl}oxy)butoxy]-[1,1'-biphenyl]-4-carboxylic acid, and addition salts thereof with a pharmaceutically-acceptable acid or base.

12. A compound of claim 1 which is selected from N-{2-[7-(4-{[4'-(hydroxymethyl)-[1,1'-biphenyl]-4-yl]oxy}butoxy)-1-naphthyl]ethyl}acetamide, and addition salts thereof with a pharmaceutically-acceptable acid or base.

13. A compound of claim 1 which is selected from N-(2-{7-[4-([1,1'-biphenyl]-4-yloxy)butoxy]-1-naphthyl}ethyl)acetamide, and addition salts thereof with a pharmaceutically-acceptable acid or base.

14. A compound of claim 1 which is which is selected from N-(2-{7-[4-([1,1'-biphenyl]-3-yloxy)butoxy]-1-naphthyl}ethyl)acetamide, and addition salts thereof with a pharmaceutically-acceptable acid or base.

15. A pharmaceutical composition comprising as active principle an effective amount of a compound of claim 1, together with one or more pharmaceutically-acceptable excipients or vehicles.

* * * * *